United States Patent
Riihinen et al.

(10) Patent No.: US 10,494,679 B2
(45) Date of Patent: Dec. 3, 2019

(54) METHOD FOR QUANTITATIVE MONITORING OF ENDOSPORES IN AQUEOUS ENVIRONMENT OF A PAPER OR BOARD MILL

(71) Applicant: Kemira Oyj, Helsinki (FI)

(72) Inventors: Kalle Riihinen, Espoo (FI); Marko Lauraeus, Nummela (FI); Marko Kolari, Vantaa (FI); Juhana Ahola, Vantaa (FI)

(73) Assignee: Kemira Oyj, Helsinki (FI)

( * ) Notice: Subject to any disclaimer, the term of this patent is extended or adjusted under 35 U.S.C. 154(b) by 190 days.

(21) Appl. No.: 15/553,999

(22) PCT Filed: Feb. 26, 2016

(86) PCT No.: PCT/FI2016/050123
§ 371 (c)(1),
(2) Date: Aug. 27, 2017

(87) PCT Pub. No.: WO2016/135387
PCT Pub. Date: Sep. 1, 2016

(65) Prior Publication Data
US 2018/0037936 A1 Feb. 8, 2018

(30) Foreign Application Priority Data
Feb. 27, 2015 (FI) .................. 20155138

(51) Int. Cl.
*C12P 19/34* (2006.01)
*C12Q 1/689* (2018.01)
*C12Q 1/24* (2006.01)

(52) U.S. Cl.
CPC ........... *C12Q 1/689* (2013.01); *C12Q 1/24* (2013.01)

(58) Field of Classification Search
CPC .................. C12Q 1/24; C12Q 1/689
See application file for complete search history.

(56) References Cited

U.S. PATENT DOCUMENTS

| | | |
|---|---|---|
| 5,928,875 A | 7/1999 | Breen et al. |
| 2004/0014122 A1* | 1/2004 | Breen .................. C12Q 1/689 435/6.15 |
| 2009/0305240 A1 | 12/2009 | Yoshida et al. |
| 2011/0318750 A1* | 12/2011 | Venkateswaran .... C12Q 1/6848 435/6.12 |
| 2012/0231961 A1 | 9/2012 | La Duc et al. |
| 2014/0155283 A1 | 6/2014 | Venkateswaran et al. |

FOREIGN PATENT DOCUMENTS

| | | |
|---|---|---|
| WO | 2013112656 A1 | 8/2013 |
| WO | 2014015044 A1 | 1/2014 |

OTHER PUBLICATIONS

Rawsthorne, H. et al. PCR-based method using propidium monoazide to distinguish viable from nonviable *Bacillus subtilis* spores. Applied and Environmental Microbiology, 2009. vol. 75, No. 9, pp. 2936-2939. p. 2936, abstract, 2nd and 3rd paragraph; p. 2937, 2nd paragraph; p. 2939, I. 1-18.

Finnis Patent and Registration Office, Search Report, FI20155138, dated Oct. 28, 2015.

* cited by examiner

*Primary Examiner* — Cynthia B Wilder
(74) *Attorney, Agent, or Firm* — Berggren LLP

(57) ABSTRACT

The invention relates to a method for quantitative monitoring of bacterial endospores in an aqueous environment of a paper or board mill. The method comprises at least the following steps: obtaining at least a first aqueous sample originating from the industrial aqueous environment; destroying bacteria in vegetative form in the first sample by a suitable treatment, preferably by heating the first sample to a desired temperature; adding intercalating agent (such as PMA) to the treated first sample and allowing it to interact (e.g. by cross-linking) with the destroyed bacteria, so that the nucleic acid from the destroyed bacteria are unavailable for PCR; and determining the endospore level in the first sample by using quantitative polymerase chain reaction (qPCR) in which only the DNA from the endospores is available for amplification.

12 Claims, No Drawings

METHOD FOR QUANTITATIVE MONITORING OF ENDOSPORES IN AQUEOUS ENVIRONMENT OF A PAPER OR BOARD MILL

PRIORITY

This application is a U.S. national application of PCT-application PCT/FI2016/050123 filed on Feb. 26, 2016 and claiming priority of Finnish national application number FI 20155138 filed on Feb. 27, 2015, the contents of all of which are incorporated herein by reference.

The present invention relates to a method for quantitative monitoring of endospores in aqueous environment of a paper mill or a board mill according to the preambles of enclosed claims.

Bacterial cells are normally present in the aqueous environments of paper and board mills. Bacterial growth in the process is commonly monitored and limited by using various measures, e.g. feeding of biocides into the processes. However, certain bacterial cells form endospores, which are highly resistant to typical bacterial destruction methods, such as heat, disinfectants, chemical biocides, desiccation, ultraviolet light and ionizing radiation. The endospores may remain viable but dormant for prolonged periods, even for years, until the external conditions become favourable, after which the transformation, i.e. germination, of bacterial endospore takes place.

Especially in production of tissue and food and/or beverage packaging board, the hygiene level of the final product is of special interest. The final end product should not contain high levels of bacterial endospores, because the endospores may contaminate the materials which come into contact with the final product, e.g. food articles which are packed into the food or liquid packaging board. For example, for food packaging board, which is used for pizza boxes, coffee cups, etc., the maximum endospore content is typically <1000 CFU/g of dry board, and there exist end uses where the maximum allowed endospore content is <250 CFU/g of dry board.

Traditionally bacterial endospores are detected by using conventional cultivation methods, which are time consuming. Typically cultivation methods provide results only after 48-72 hours after the sampling. It is understandable that in continuous production of paper or board this delay is not optimal. For example, timely adjustment of spore control biocide program towards changing process conditions is not possible as the follow up cultivation results are obtained only after the above specified delay. This makes the biocide feeding unnecessary complicated and hard to optimise. Therefore there exists a need for fast monitoring of bacterial endospores in aqueous processes of paper or board mills.

An object of this invention is to minimise or possibly even eliminate the disadvantages existing in the prior art.

Another object of the present invention is to provide a fast and cost-effective method for quantitative monitoring of bacterial endospores in aqueous environment of paper or board mill.

These objects are attained with the invention having the characteristics presented below in the characterising parts of the independent claims.

Some preferred embodiments of the invention are presented in the dependent claims.

A typical method according to the present invention for quantitative monitoring of bacterial endospores in an aqueous environment of a paper or board mill, comprises at least the following steps:

obtaining at least a first aqueous sample originating from the aqueous environment, destroying bacteria in vegetative form in the first sample by suitable treatment, preferably by heating the first sample to a desired elevated temperature, adding intercalating agent to the treated first sample and allowing it to interact with the destroyed bacteria, and determining the endospore level in the first sample by using quantitative polymerase chain reaction (qPCR).

Now it has been surprisingly found that by using a method comprising the step of destruction of vegetative bacteria, interaction with intercalating agent and real-time quantitative polymerase chain reaction (qPCR), it is possible to obtain rapid determination of bacterial endospore level in a sample originating from a production of paper or board. The monitoring method gives a reliable determination result for the endospore level in the aqueous environment of a paper or board mill. The method according to present invention thus provides a possibility to quickly detect endospore outbursts caused by unexpected changes in the process conditions, such as pH or redox fluctuations. In this manner the production of poor quality products, e.g. packaging grade paper or board can be minimized. Furthermore, it is possible to avoid erroneous biocide feeding to the process, i.e. feeding of a non-killing biocide dosage, which may initiate endospore formation due to e.g. oxidative stress.

In the present context the term "endospore" is understood as dormant and non-reproductive structure formed by bacteria. Endospore comprises bacterium's DNA and a part of its cytoplasm encased by a protective outer covering. Endospore can germinate to the metabolically active state, i.e. vegetative state, under favourable conditions.

According to the present invention at least a first aqueous sample is obtained or taken from aqueous environment of a paper or board mill. The sample size is typically in the range of 10-100 ml, preferably 20-30 ml, and normally the availability of the sample is not a limiting factor. As an example it can be given that in certain paper and board manufacturing processes where it is desired to maintain the total endospore content at very low level, such as <1000 CFU/ml by using high biocide dosages, a sample size of 100 ml may be used. On the other hand, in process waters where the bacterial cell content may be at high level, i.e. about level of $10^8$ CFU/ml, the sample size of 25 ml may be considered more practical.

The sample may comprise cellulosic fibres and/or fibrils, and have a solid content up to 2-8 weight-%. The sample normally comprises also a variety of chemicals and/or compounds used in paper or board making, such as starch; inorganic filler particles; synthetic polymers, such as polyacrylamide.

In the beginning of the present method bacteria in vegetative form is destroyed by using suitable treatment. The suitable treatment may be a physical treatment where the sample is subjected to e.g. radiation, such as UV or heat, or a chemical treatment, where the sample is subjected to a suitable biocide at dosage level that destroy the bacteria in vegetative form but does not interfere with the performance of the intercalacting agent during the succeeding process steps. According to one preferred embodiment the first sample is heated to a desired elevated temperature of at least 60° C., preferably for at least 70° C., more preferably at least 75° C. The maximum temperature used is typically 100° C., preferably 80° C. The sample is kept at elevated temperature for at least 10 min, preferably at least 15 min, more preferably at least 20 min. In other words, one preferable way to destroy the bacteria in vegetative form is to heat the sample to a temperature in the range of 75-80° C. and keep the sample in this elevated temperature for 15-60 min, preferably for 20-40 min. Various heat treatment processes are known in the art, both at normal atmospheric pressure and at increased pressure. In a preferred embodiment the heat treatment step is an easy, rapid and practical at field and/or industrial conditions, where it can be performed by using a water bath at normal pressure. The heating of the first sample to the elevated temperature defined above produces pasteurisation of the sample and disrupts the vegetative bacterial cells which are present in the sample. After the heating the sample comprises disrupted, i.e. killed and destroyed, vegetative bacterial cells and typically unaffected bacterial endospores.

Before the destruction step, preferably by heating, the first sample may optionally but preferably be filtered in order to separate unwanted solid particular material, such as solid particles, fibres, fibrils or the like, from the liquid phase of the sample. This preliminary filtration for separation of unwanted solid particular material is typically fast and performed e.g. by Buchner funnel, by using a filter with about 3 mm openings.

According to one embodiment of the invention the first sample is filtered after the destruction step, in order to separate the destroyed vegetative bacterial cells as well as the endospores from the liquid phase of the sample. Filtration may be performed by using a filter with e.g. 0.4 µm openings. The bacterial cells and endospores are collected and/or attached onto the filter, which simplifies the further processing of the treated first sample.

An intercalating agent is added to the treated first sample, preferably after the above described filtration step, and the agent is allowed to interact with the destroyed bacterial cells. According to one embodiment of the invention the intercalating agent is selected from propidium monoazide (PMA), ethidium monoazide (EMA), ethidium bromide, berberine, proflavine, daunomycin, doxorubicin and thalidomide. The preferred intercalating agent is propidium monoazide (PMA). Intercalating agent is preferably added to the treated first sample in such amount that all DNA from the destroyed bacterial cells interacts with the intercalating agent. Thus it is possible to guarantee that no DNA from the vegetative bacterial cells is multiplied in the following qPCR step and they do not produce a signal in the qPCR step. However, an unnecessary exaggerated excess addition of intercalating agent is preferably avoided, because it may produce a risk that the intercalating agent diffuses into the endospores and begin to interact with the endospore DNA. Typically intercalating agent is added to the sample in amount that provides an intercalating agent concentration of <100 µM, preferably in the range of 10-90 µM, more preferably 25-75 µM, even more preferably 40-60 µM.

The first sample is allowed to incubate in the dark after the addition of the intercalating agent. The incubation time is in the range of 1-30 minutes, preferably 2-10 minutes, more preferably 4-6 minutes. The intercalating agent is able to crosslink DNA double strands from the destroyed bacterial cells covalently when exposed to intense blue light, preferably having a wavelength of about 400-500 nm, at room temperature. The blue light can be produced, for example, by using a light-emitting diode, LED. The exposure time may be 1-30 minutes, preferably 2-10 minutes, more preferably 4-6 minutes.

The sample is preferably not dried before the addition of the intercalating agent. This means that the method is preferably free from drying of the sample.

Preferably the time delay between the destruction step and the addition of the intercalating agent is as short as practically possible.

After the first sample has been allowed to interact with the intercalating agent the endospore level is determined in the first sample by using quantitative polymerase chain reaction, qPCR. The DNA from the endospores is extracted and multiplied by using qPCR. An example of suitable DNA extraction for cells isolated from the material is described by Rinttilä et al., Development of an extensive set of 16S rDNA-targeted primers for quantification of pathogenic and indigenous bacteria in faecal samples by real-time PCR. J. Appl. Microbiol. 2004; 97(6):1166-1177. In the exemplary procedure, lysis reagents are added to the tube with glass beads and FastPrep bead beater is used three times at speed of 6.5 m/s for 1 minute. The tubes are incubated at 65° C. for 20 min, vortexing with Thermomixer every 2 minutes. 800 µl of phenol-chloroform-isoamylalcohol (24:23:1) is added, mixed and centrifuged at 10000 g for 5 min. 600 µl of liquid phase is transferred into a new tube and extracted with chloroform:isoamylalcohol (24:1). 270 µl 100% isopropanol is used to precipitate the DNA and the liquid is removed after centrifugation of 20000 g at +4° C. for 15 min. Pellet is washed twice with 1 ml (−20° C.) 70% EtOH and centrifuged with 20000 g at +4° C. for 5 minutes. After centrifugation, the pellet is dried in vacuum excicator at +45° C. for 20 minutes and dissolved into 45 µl of Tris-EDTA buffer at +55° C. for 1.5-2 hours. Suitable qPCR methods and procedures are known as such for a person skilled in the art and commercially available. An example of a suitable qPCR method is described by Makinen, R. et al., Can. J. Microbiol. 59: 407-412 (2013). In the exemplary method the amount of 16S rRNA gene copies is measured with ABI SDS 7000 (Applied Biosystems, UK) by using SYBR Green I (Roche Diagnostics, Germany) as the fluorescent reporter. A person skilled in the art possesses knowledge of other suitable DNA extraction and/or qPCR procedures.

According to one embodiment of the invention at least a second aqueous sample is obtained or taken from the same aqueous environment. Preferably the first and the second sample are taken at the same time, more preferably both the first and the second sample originate from one single original sample, which have been divided into first, second, and possible successive samples for determination of endospore level in the aqueous environment.

The amount of vegetative bacteria, i.e. vegetative bacterial cells, is determined directly from the second sample, preferably after a prefiltration step, by using quantitative polymerase chain reaction, qPCR. The second sample is not subjected to any destruction step, e.g. by heat-treatment, or interaction with an intercalacting agent.

The determined endospore level from the first sample is then compared to the determined amount of vegetative bacterial cells in the second sample. In this manner it is possible to obtain information about the total amount of vegetative bacterial cells in the aqueous environment of a paper or board mill and their proportion to the level of endospores in the same environment.

According to one preferable embodiment of the invention the obtained information about the total amount of vegetative bacterial cells and the amount of endospores is used for prompt adjustment of biocide feeding regime for endospore control in paper or board making production. The information is able to provide valuable knowledge and insight about the bacterial conditions of the aqueous environment in the paper or board mill, and the knowledge can be used, for example, for determining the correct biocide feeding regime, to spot problematic areas of the process, and/or to detect high and/or fluctuating spore levels. In other words, according to a preferable embodiment of the invention at least one biocide is fed to the aqueous environment, and the amount of the fed biocide is determined on the basis of the determined endospore level.

The present invention enables use of effective biocides, which may otherwise be too expensive for continuous use, as the biocide dosage and timing can be accurately determined based on information about the amount of bacterial spores and vegetative bacterial cells in the process. The biocide may be, for example, oxidizing or non-oxidizing biocide. On basis of the obtained determination results the biocide dosages in one or several critical process locations are adjusted to a level that reduces the level of endospores in the produced paper/board <1000 CFU/g of dry paper/board, alternatively <250 CFU/g of dry paper/board.

The total time from the start of the destruction step to the end of the qPCR step may be less than 24 h, preferably 6-24 h, more preferably 7-9 h. This means that the biocide efficacy follow up by using the present method can be performed daily, or even several times a day. The method according to the invention is preferably performed on-site.

According to one embodiment of the invention the method is used for monitoring of endospores e.g. from *Bacillus, Brevibacillus* and/or *Paenibacillus*, which are known to grow in the process conditions of a paper or board machine. These genera are capable of producing thermotolerant endospores, which are resistant to the heat of the dryer section of a paper or board machine. Therefore the present invention provides good possibility to monitor the endospore level of these genera and to start specific and correct biocide feeding.

According to one preferable embodiment of the invention the method is used for production of food and/or liquid packing grade paper or board. Typically the grammage of the packaging grade board may be 150-400 g/m$^2$, preferably 200-360 g/m$^2$, more preferably 240-300 g/m$^2$. The paper and board grades for food and/or liquid packaging are often polymer coated or foil-laminated for barrier properties. Suitable polymers for coating are, e.g. polyolefins, such as polyethylene or polypropylene; polyvinyl alcohol; polyvinylamine; polyethylene terephthalate; polybutylene terephthalate.

EXPERIMENTAL

Some embodiments of the invention are described in the following non-limiting examples.

Example 1

This on-site trial was performed at an alkaline paper machine, which produces 3-ply food packaging board, in order to follow-up performance of spore control biocide program. Two sampling rounds, one in the morning and one in the afternoon, were performed at three process locations; in the outlets of broke tower, birch pulp tower and pine pulp tower.

First 1 litre of each process sample was first filtrated by using a Buchner funnel with 3 mm pore size in order to remove fibers and solids from the sample. After this the obtained filtrate was divided into six 50 ml Falcon tubes; 3 parallel samples were heat treated for 15 min at 80° C. in order to kill vegetative bacterial cells, and 3 parallel samples were left non-treated. After this all 6 parallel samples were filtrated through 0.4 µm filter papers. The filtered heat treated samples were stained with PMA (50 µM, 1 ml) with 5 min contact time in dark followed by 5 min exposure to blue LED light. After this DNA of both the treated samples as well as the non-treated samples were analyzed by using DNA extraction and qPCR method as follows.

In brief, lysis reagents were added to the tube with glass beads and FastPrep bead beater was used three times at speed of 6.5 m/s for 1 minute. The tubes were incubated at 65° C. for 20 min, vortexing with Thermomixer every 2 minutes. 800 µl of phenol-chloroform-isoamylalcohol (24:23:1) was added, mixed and centrifuged at 10000 g for 5 min. 600 µl of the liquid phase was transferred into a new tube and extracted with chloroform:isoamylalcohol (24:1). 270 µl of 100 isopropanol was used to precipitate the DNA and the liquid was removed after centrifugation of 20000 g at +4° C. for 15 min. Pellet was washed twice with 1 ml (−20° C.) of 70% EtOH and centrifuged with 20000 g at +4° C. for 5 minutes. After centrifugation, the pellet was dried in vacuum excicator at +45° C. for 20 minutes and dissolved into 45 µl of Tris-EDTA buffer at +55° C. for 1.5-2 hours. The DNA was analyzed with qPCR. The amount of 16s rRNA gene copies were measured with ABI SDS 7000 (Applied Biosystems, UK) by using SYBR Green I (Roche Diagnostics, Germany) as the fluorescent reporter. Total 16s rRNA genes represent total bacteria, and Bacilli 16s rRNA genes endospore forming bacteria.

As a reference, total aerobic bacteria and bacterial spore counts were measured by using conventional cultivation methods (plate count agar, +45° C./+37° C., 2 days incubation) at an external laboratory. Prior to bacterial spore determination, samples were pasteurized at +80° C. for 20 min. Results are shown in Table 1.

TABLE 1

Results for Example 1.

| | Total aerobic bacteria (untreated samples) | | | Bacterial spores (heat treated and stained samples) | |
|---|---|---|---|---|---|
| | | Method of Invention | | | Method of Invention |
| | Cultivation method CFU/ml | Total 16s rRNA genes/ sample | Bacilli 16s rRNA genes/ml | Cultivation method CFU/ml | Bacilli 16s rRNA genes/ml |
| morning samples | | | | | |
| Broke tower | <100 | <5 × 10$^3$ | <2 × 10$^3$ | <10 | <2 × 10$^3$ |
| Birch pulp | <100 | 6 × 10$^3$ | 5 × 10$^3$ | <10 | <2 × 10$^3$ |
| Pine pulp | <100 | 8 × 10$^3$ | 2 × 10$^3$ | <10 | <2 × 10$^3$ |
| afternoon samples | | | | | |
| Broke tower | <100 | <5 × 10$^3$ | <2 × 10$^3$ | <10 | <2 × 10$^3$ |
| Birch pulp | <100 | 2 × 10$^4$ | 4 × 10$^3$ | <10 | <2 × 10$^3$ |
| Pine pulp | <100 | 6 × 10$^3$ | <2 × 10$^3$ | <10 | <2 × 10$^3$ |

Obtained results from cultivation method indicate that microbiological status of the process was at good level during the sampling day, as total aerobes (<100 CFU/ml) and endospores (<10 CFU/ml) were both below detection limit. Moreover, Bacilli 16s rRNA genes were not found in the heat treated and stained samples, thus results from the method of invention indicate that endospores were not present in the process during the sampling day. This good microbiological situation in the process was seen also in the final board; aerobic spore counts in the final board were below 250 CFU/g of produced board (results not shown). Interestingly, obtained results from incoming pulp towers showed some ($2 \times 10^3$-$5 \times 10^3$) Bacilli 16s rRNA genes, thus both these pulp towers contained Bacilli bacteria which may produce endospores in unfavorable growth conditions, such as in case of sudden pH or redox shock. Thus the described method of invention can effectively be used to monitor microbiological quality of critical process points, and to rapidly, i.e. within a working day, detect potential spore formation. This enables an economically feasible way to adjust spore control biocide program, and eventually to minimize production of spore contaminated board, and finally less recalls for board manufacturer.

Example 2

Microbiological on-site follow-up trial was performed at an alkaline paper machine producing 3-ply folding box board, in order to follow up the performance of current biocide program against spore forming bacteria in broke tower. Altogether six sampling rounds were performed from the outlet of Broke tower.

The process samples were handled and processed as described in Example 1. Results are shown in Table 2.

Obtained results from Table 2 show that broke tower contained much bacteria; total aerobic bacteria counts varied between $5 \times 10^6$-$1 \times 10^7$ CFU/ml, total 16s rRNA genes between $5 \times 10^7$-$3 \times 10^8$ and Bacilli 16s rRNA genes between $1 \times 10^6$-$4 \times 10^7$ during all three sampling days. Results thus indicate that additional biocides would be required in order to effectively control total bacteria and Bacilli population in broke tower. Interestingly, amount of Bacilli 16s rRNA genes was high ($1 \times 10^6$-$4 \times 10^7$) in all untreated samples indicating that much vegetative cells were present in the broke tower. However, Bacilli 16s rRNA genes varied markedly between low ($2 \times 10^2$) to high ($2 \times 10^6$) in the heat treated and stained samples, which indicate that mature spore levels fluctuated in the broke tower. Sporulation tendency of Bacilli population, that is new spore formation, is known to be highly regulated and depended on process conditions. Obtained results from traditional cultivation results did not reveal such a sporulation potential, since detected spore counts varied between <10 to 300 spores/ml. By using the described method of invention, it is possible to follow microbiological status in critical process points and detect rapidly, i.e. within a working day, new spore formation in the process. This enables effective and economically feasible spore control in the process, minimized production of spore contaminated board, and finally less recalls for board manufacturer.

TABLE 2

Results for Example 2.

| Broke Tower sampling | Total aerobic bacteria (untreated samples) | | | Bacterial endospores (heat treated and stained samples) | |
|---|---|---|---|---|---|
| | Cultivation method CFU/ml | Method of Invention | | Cultivation method CFU/ml | Method of Invention |
| | | Total 16s rRNA genes/ sample | Bacilli 16s rRNA genes/ml | | Bacilli 16s rRNA genes/ml |
| $7^{th}$ Oct, morning | $7 \times 10^6$ | $3 \times 10^8$ | $4 \times 10^7$ | $3 \times 10^2$ | $2 \times 10^6$ |
| $7^{th}$ Oct, afternoon | $5 \times 10^6$ | $2 \times 10^8$ | $3 \times 10^7$ | $5 \times 10^1$ | $1 \times 10^5$ |
| $5^{th}$ Nov, morning | $8 \times 10^6$ | $1 \times 10^8$ | $2 \times 10^6$ | $2 \times 10^1$ | $6 \times 10^4$ |
| $5^{th}$ Nov, afternoon | $1 \times 10^7$ | $2 \times 10^8$ | $1 \times 10^6$ | $2 \times 10^1$ | $1 \times 10^4$ |
| $11^{th}$ Nov, morning | $6 \times 10^6$ | $5 \times 10^7$ | $1 \times 10^6$ | <10 | $2 \times 10^2$ |
| $11^{th}$ Nov, afternoon | $5 \times 10^6$ | $9 \times 10^7$ | $9 \times 10^6$ | $2 \times 10^1$ | $1 \times 10^3$ |

Example 3

This laboratory test was performed in order to evaluate efficacy of spore control biocide against authentic bacterial population in broke sample taken from an alkaline paper machine producing 3-ply food packaging board. The first broke sample was stored as such and the second broke sample with 150 ppm dosage of tested spore control biocide. Storage took place at +45° C., without mixing. Total aerobic bacteria and aerobic spore counts were determined by using conventional cultivation methods (plate count agar, +45° C./+37° C., 2 days incubation) at the beginning of the test (untreated) and after 3 days contact time (treated and untreated samples), along with pH and redox measurements.

Results are shown in Table 3.

TABLE 3

Results for Example 3.

| | Start of the test | | | | 3 days contact time | | | |
|---|---|---|---|---|---|---|---|---|
| | Total aerobic bacteria (CFU/ml) | Bacterial spores (CFU/ml) | pH | redox (mV) | Total aerobic bacteria (CFU/ml) | Bacterial spores (CFU/ml) | pH | redox (mV) |
| Untreated broke sample | $3 \times 10^7$ | <10 | 8.2 | 134 | $3 \times 10^7$ | $5 \times 10^3$ | 6.5 | −107 |
| Biocide treated broke sample | ND | ND | ND | ND | <100 | <10 | 7.3 | 83 |

Obtained results show that strong spoilage occurred in the untreated broke sample during 3 days contact time; total aerobic bacteria counts were at high ($3 \times 10^7$ CFU/ml) and level of aerobic spores increased up to $5 \times 10^3$ CFU/ml. Moreover, pH (8.2→6.5) and redox (134 mV→−107 mV) dropped markedly. On the contrary, the 150 ppm dosage of tested spore control biocide, preserved broke sample effectively; total aerobic bacteria (<100 CFU/ml) and bacterial spores (<10 CFU/ml) remained below detection limit, and pH (7.3) as well as redox (83 mV) values remained at good level. Results thus indicate that the tested spore control biocide, as 150 ppm dosage, can be used to control new spore formation in broke. Based on literature and own laboratory results (data not shown) it is known that such a treatment is non-effective in killing mature bacterial spores. For effective spore control in paper making process, it is thus economically more feasible to control new spore formation in the process than try to kill mature spores.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for quantitative monitoring of bacterial endospores in an aqueous environment of a paper or board mill, the method comprising at least the following steps:
   obtaining at least a first aqueous sample and at least a second aqueous sample originating from an industrial aqueous environment,
   destroying bacteria in vegetative form in the first sample by heating the first sample to a desired temperature,
   adding intercalating agent to the heated first sample and allowing it to interact with the destroyed bacteria,
   determining the endospore level in the first sample by using quantitative polymerase chain reaction (qPCR),
   determining the amount of bacterial cells in vegetative form in the second sample by using qPCR, and
   comparing the determined endospore level from the first sample to the determined amount of vegetative bacterial cells in the second sample and using the obtained information for adjustment of biocide feeding regime for endospore control in paper or board making process.

2. The method according to claim 1, wherein at least one biocide is fed to the aqueous environment, and the amount of the fed biocide is determined on a basis of the determined endospore level.

3. The method according to claim 1, wherein the destroying of bacteria in vegetative form is performed by heating the first sample to a desired temperature of at least 60° C., for at least 70° C., or at least 75° C.

4. The method according to claim 1, wherein the first sample is filtered before the destruction step, by heating, in order to separate solid particulate material from the sample.

5. The method according to claim 1, wherein the intercalating agent is selected from propidium monoazide (PMA), ethidium monoazide (EMA), ethidium bromide, berberine, proflavine, daunomycin, doxorubicin and thalidomide, or from propidium monoazide (PMA).

6. The method according to claim 1, wherein the intercalacting agent is added in a concentration of <100 µM, in a range of 10-90 µM, 25-75 µM, or 40-60 µM.

7. The method according to claim 1, wherein the first sample is allowed to incubate in the dark after the addition of the intercalating agent for 1-30 minutes, 2-10 minutes, or 4-6 minutes.

8. The method according to claim 7, wherein the incubated first sample is exposed to light having a wavelength of about 400-500 nm, for 1-30 minutes, 2-10 minutes, or 4-6 minutes.

9. The method according to claim 1, wherein the total time from the start of the destruction step to the end of the qPCR step is less than 24 h, 6-24 h, or 7-9 h.

10. The method according to claim 9, further comprising using bacterial endospores from *Bacillus, Brevibacillus* and/or *Paenibacillus*.

11. The method according to claim 1, further comprising using the quantitative method for monitoring of the bacterial endospores for production of food and/or liquid packing grade paper or board.

12. The method according to claim 11, further comprising producing a packaging grade board having a grammage of 150-400 $g/m^2$, 200-360 $g/m^2$, or 240-300 $g/m^2$.

* * * * *